Figure 1:
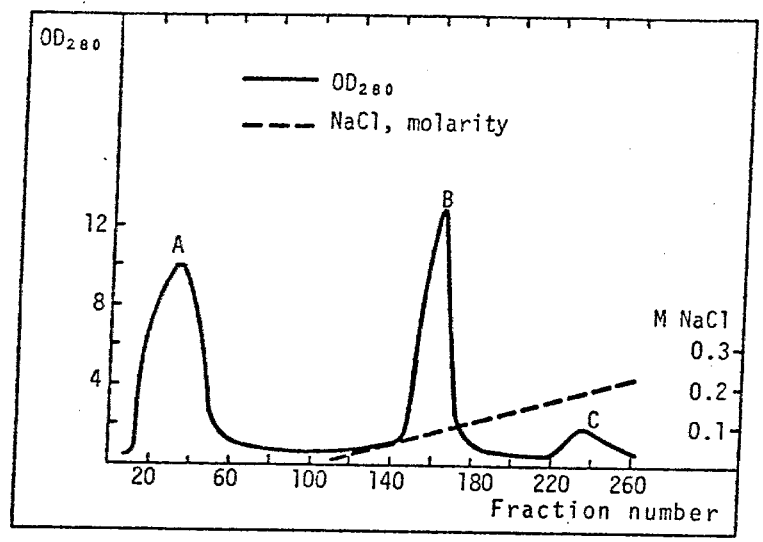

United States Patent [19]

Tang et al.

[11] 4,266,031

[45] May 5, 1981

[54] PROTEASE PRODUCT OF REDUCED ALLERGENICITY

[75] Inventors: Peter Tang; Grethe C. Nielsen, both of Tåstrup; Keith Gibson, Vaerloese; Knud Aunstrup, Farum; Hans Schiff, Soeborg, all of Denmark

[73] Assignee: Novo Industri A/S, Denmark

[21] Appl. No.: 54,555

[22] Filed: Jul. 3, 1979

[30] Foreign Application Priority Data

Jul. 4, 1978 [GB] United Kingdom ............... 28773/78

[51] Int. Cl.³ ........................... C12N 9/96; C12N 9/56
[52] U.S. Cl. .................................... 435/188; 435/172; 435/222; 435/836
[58] Field of Search ............... 435/172, 187, 188, 222, 435/221, 836

[56] References Cited

U.S. PATENT DOCUMENTS 3,748,233   7/1973   Viccaro ................................ 435/222

FOREIGN PATENT DOCUMENTS 2063988   7/1972   Fed. Rep. of Germany .
2061067   6/1971   France .
2075637  10/1971   France .
1263765   2/1972   United Kingdom .

OTHER PUBLICATIONS

Keay, Fermentation Technology Today, Proc IV Int. Ferment Symp., Mar. 19-25, 1972, Kyoto, Japan, pp. 289-295.
Methods in Enzymology, vol. 19, pp. 199-215 (1970), article by Ottesen et al entitled The Subtilisins.

Primary Examiner—Lionel M. Shapiro
Attorney, Agent, or Firm—Fidelman, Wolffe & Waldron

[57] ABSTRACT

A novel protease product suitable for admixture to washing compositions and exhibiting substantially attenuated allergenic properties is prepared by cultivating strains of *Bacillus licheniformis* which have been mutated to block their synthesis of protease other than Subtilopeptidase A (subtilisin). The commercial *Bacillus licheniformis* derived protease products are mixtures of subtilisin and a non-serine protease of lower stability and greater allergenicity than subtilisin.

6 Claims, 4 Drawing Figures

PROTEASE PRODUCT OF REDUCED ALLERGENICITY

This invention relates to a *Bacillus licheniformis* derived protease preparation having substantially reduced allergenic properties and being useful as a commercial protease product, for example for admixture into detergent compositions, such as washing powder compositions for domestic use.

BACKGROUND OF THE INVENTION

Commercial detergent protease preparations are commonly obtained by cultivation of selected strains of *Bacillus licheniformis*. The protease is elaborated extracellularly by the microorganism and a protease concentrate is subsequently recovered from the culture broth, e.g. by precipitation with salts and/or solvents. The work-up procedures may be conducted in such a manner that practically no protease activity is left in the culture broth. However, the recovery procedure is not particularly specific with respect to the protease, and in consequence, the protease concentrate will also normally contain broth constituents other than the enzyme. To produce a commercial detergent protease product, such as Alcalase supplied by Novo Industri A/S, Denmark (Alcalase being a Registered Trade Mark), the protease concentrate is then admixed with an inert filling material and the auxiliary agents which serve to produce a low dusting protease product of a predetermined proteolytic activity.

By far the most predominant proteolytic component of commercial *Bacillus licheniformis* derived protease products, such as Alcalase, has been identified as subtilopeptidase A (EC 3.4.21.14), hereinafter called subtilisin. This enzyme, which can be recovered from the commercial product in purified and crystallized form has been characterized in great detail and was found to belong to the same group of so-called serine proteases as trypsin and chymotrypsin. The enzyme nomenclature alludes to the fact that originally the microbial source of Alcalase had been classified as *B. subtilis*. However, it should now be generally accepted that the Alcalase producing microorganism is *B. licheniformis*.

Practically all proteins, including industrial enzymes, exhibit allergenic properties of varying potency, depending on the individual protein. A significant allergenic effect of *Bacillus licheniformis* derived protease preparations was experienced early after their commercial introduction and ever since then such allergenicity has been regarded by the art as an inherent inconvenience connected with the use of the protease products.

Heretofore, efforts to minimize the incidence of hypersensitive reactions among workmen and users have been directed solely towards providing low dusting particulate, e.g. granular or encapsulated, protease products so as to reduce the risk of exposure to the protease, both by workers in detergent enzyme and in washing powder manufacturing plants and by users of household washing powders. The success of these endeavours is, in part, evidenced by the continued widespread domestic use of detergent enzyme containing washing powders.

However, it is also known that the development of allergic reactions can be very unpredictable and capricious. Thus, there yet remains a need for a commercial protease preparation of allergenic properties substantially attenuated as compared with those preparations known heretofore.

It is an object of the present invention to provide a *B. licheniformis* protease product attenuated in allergenicity.

It is another object of the present invention to provide an industrially feasible process for preparing a product having reduced allergenicity.

The attainment of these objects is based on certain observations relating to the constituents of commercial protease preparations and to their properties.

Recently published investigations by means of qualitative (but highly sensitive), immunoelectrophoresis (e.g. according to Grabar-Williams, vide R. Verbruggen et al. Biochim, Biophys, Acta, vol. 365 (1974), pp. 108–114) indicated that commercially available protease products, notably Alcalase are antigenically heterogeneous.

In subsequent studies published by Verbruggen (Biochem. Journal, vol. 151 (1975), pp. 149–155), using the technique of quantitative crossed agarose gel immunoelectrophoresis, it was found that the main protease component of Alcalase, consisting of a family of subtilisin isoenzymes, is accompanied by a minor protein component, which is antigenically different from the main protease component.

RATIONALE OF THE INVENTION

One approach towards further elucidating the composition of commercial protease preparations, which is also applicable on a preparative laboratory scale for fractionating such preparations is to subject the protease concentrate recovered from the culture broth to ion exchange chromatography. Thus, for example, a *B. licheniformis* protease concentrate (30 g) was chromatographed on a column (5×35 cm) of carboxymethyl cellulose (CMC, 500 g) maintained at 4° C. and equilibrated with a buffer of pH 6.5 consisting of 0.005 M tris(hydroxymethyl)amino methane (TRIS) maleate and 0.002 M calcium acetate. Elution was conducted with the same buffer, applying a linear sodium chloride gradient subsequent to the emergence of the front peak. The optical density of fractions (20 ml), collected at a flow rate of 210 ml/h, was monitored at 280 nm. The chromatogram is shown in FIG. 1 of the accompanying drawings.

The major protease component recovered from pooled fractions corresponding to peak B of the chromatogram, was identified as subtilisin. It is believed that the minor protease component represented by peak C is identical to the minor protein component detected in crossed immunoelectrophoresis (vide supra) and described as being antigenically different from the main component, but not otherwise characterized. Hereinafter the minor protease component, identified above, will be termed "component C". Component C has been found to constitute from about 5 to about 15 percent of the total protease content of Alcalase.

Figure 2:
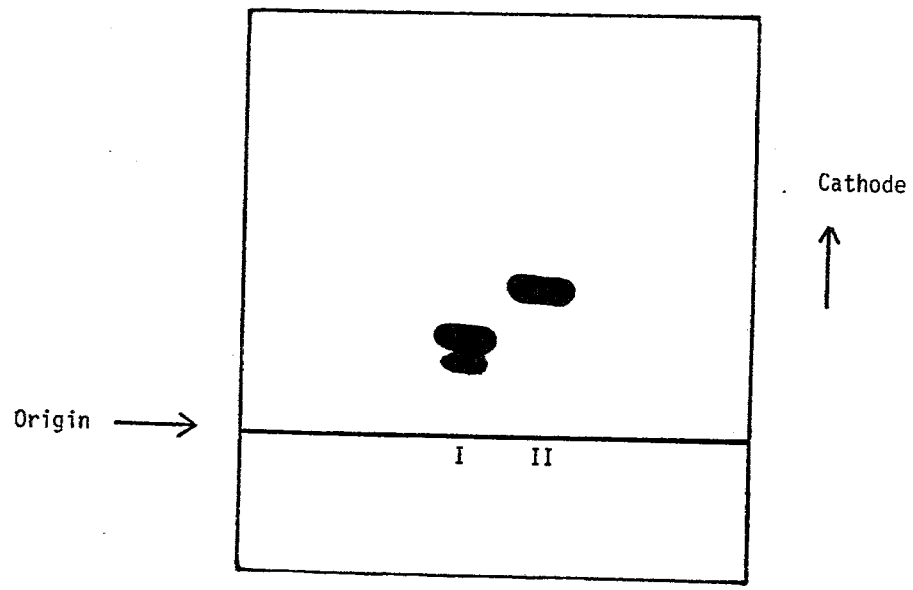

As a means of further characterization, the subtilisin component and component C, as obtained from pooled fractions corresponding to peaks B and C, respectively, were subjected to agarose gel electrophoresis. The electrophoresis was conducted in 0.075 M sodium barbital buffer of pH 8.0 at 10° C. for 60 minutes, using a voltage gradient of 15 V/cm. The samples were applied as 1% w/v solutions. The electropherograms shown in FIG. 2 of the accompanying drawings demonstrate that, under the test conditions, subtilisin (position I) and component C (position II) exhibit distinctly different cathodic migration rates.

Furthermore, the electropherograms indicate that, since both proteases migrate as band patterns, each being composed of a major band accompanied by slower migrating side bands, both the subtilisin component and component C are multiple isoenzyme systems (Verbruggen, vide supra).

Inhibition studies to be outlined later in this specification have demonstrated that, contrary to subtilisin, component C is a non-serine protease.

The present invention is based on the discovery that the allergenic potency of the subtilisin component is considerably lower than the allergenic potency of component C.

DESCRIPTION OF THE INVENTION

According to one aspect of the present invention there is provided a protease preparation suitable for admixture to washing compositions, having incorporated therein a *B. licheniformis* derived protease concentrate,, characterized in that said protease concentrate, stabilized by non-proteolytic culture broth derived peptides therein, such peptides being at least 0.5 percent by weight of the protease concentrate, is essentially free of non-serine protease and exhibits substantially attenuated allergenic properties as compared with a non-serine protease containing protease concentrate.

The protease concentrate will generally derive at least 99 percent of its proteolytic activity from the subtilisin isoenzyme system and will contain at least about 2 percent of non-proteolytically active peptides therein.

According to a further aspect of the present invention there is provided a process for preparing a protease concentrate suitable for incorporation into the protease preparations adopted for admixture into washing compositions, said protease concentrate being essentially free of non-serine protease and exhibiting substantially attenuated allergenic properties as compared with a non-serine protease containing concentrate, characterized in that a strain of *B. licheniformis*, mutated to essentially block its capability of synthesizing other proteases than subtilisin, is cultivated in a nutrient medium containing assimilable sources of carbon, nitrogen and phosphorus, followed by recovery of the protease concentrate comprising subtilisin and culture broth derived peptides.

Such recovery methods are well established in the art. Usually, the culture broth is filtered, centrifuged or otherwise clarified followed by precipitation of the protease concentrate, for example by addition of a water-soluble inorganic salt, such as sodium or ammonium sulphate or by adding a water-miscible organic solvent, such as ethanol or acetone. The precipitate may be recovered by conventional means, such as filtration or centrifugation.

The moist protease precipitate may be dried by conventional methods, for example under vacuum. A particularly advantageous large-scale drying process, combining spray drying with a subsequent drying step under fluid bed conditions, is disclosed in British Pat. No. 1,360,969.

Conversion of the dried enzyme concentrate into a commercial particulate low dusting protease preparation of predetermined activity can be performed by various methods known in the art. One method is described in British Pat. No. 1,338,249 in which substantially spherical beads are produced from a mixture of the protease concentrate and a water-dispersible solid waxy binder material, such as a non-ionic detergent. Reference is also made to British Pat. No. 1,362,365 disclosing a process whereby a moistened pre-mix of the enzyme concentrate and a solid diluent, such as sodium chloride, optionally in the presence of a binder, e.g. dextrin and/or polyethylene glycol, is extruded and then spheroidized, for example by means of an apparatus sold under the trade mark Marumerizer, and finally dried under fluid bed conditions.

Alternatively, a granular enzyme product may be produced by the process described in U.S. Pat. No. 4,106,991. A subsequent coating process may optionally be applied to further reduce the dusting properties of the final product. Coating of the particulate product is usually conducted by means of a melted wax, preferably polyethylene glycol, optionally followed by powdering the resulting coated product with a finely comminuted colouring agent, for example $TiO_2$ admixed with auxiliary powdering agents.

The present invention also provides mutant strains of *B. licheniformis* blocked as regards synthesis of component C whilst retaining the ability to synthesize subtilisin.

In addition, the present invention provides a washing composition containing an effective amount of *B. licheniformis* derived protease product which is essentially free of protease component C.

In addition to the enzyme the commercial washing powder composition of the present invention will generally contain:

(a) At least one surfactant which may be anionic, non-ionic, or amphoteric, or a water-soluble soap. Typically, an anionic surfactant (e.g. a linear alkyl aryl sulphonate) is used in admixture with a non-ionic (e.g. an alkyl phenyl polyglycol ether) in amounts of 5–30 and 1–5 percent by weight, respectively, of the washing composition.

(b) One or more builders, preferably having a concomitant sequestering function. Sodium tripolyphosphate, sodium citrate, sodium silicate, and zeolites are examples of such compounds, usually constituting from 10 to 70 percent by weight of the detergent composition.

(c) A bleaching agent, preferably a peroxy compound such as sodium perborate, typically incorporated in an amount up to 30 percent by weight of the composition.

(d) Ancillary agents, such as carboxymethyl cellulose, optical brighteners and perfumes. If required, a pH-adjusting agent is added to give a pH of the laundering medium in the range of from 8.0 to 10.5.

The particulate protease preparation of the invention is added in an amount calculated to give a protease activity of at least 0.1 Anson units (AU, vide infra), preferably 0.5–2.5 AU per 100 g of washing composition. If required, balance to 100 percent may be established with an inorganic filler, preferably sodium sulphate.

Liquid detergent compositions may be prepared from enzyme slurries, preferably in non-aqueous media. Typically, such slurries may consist of a suspension of finely ground protease concentrate in a liquid non-ionic surfactant, for example Tergitol 15 S 9 or a mixture of such surfactants. Usually, the slurry will also contain one or more inorganic fillers, such as finely ground sodium chloride, optionally in admixture with a suspension stabilizer, for example fumed silica (Aerosil 200). Tergitol and Aerosil are trade marks.

The protease slurry of the invention is added in an amount calculated to give a protease activity of at least 0.1 AU, preferably 0.5–2.5 AU per 100 g of liquid detergent composition.

The washing compositions may be prepared in the usual manner, for example by mixing together the components. Alternatively, a pre-mix is made, which is then mixed with the remaining ingredients.

DISCUSSION OF THE INVENTION

A purified grade of subtilisin, for example one which is recoverable from pooled fractions corresponding to peak B of the CMC ion exchange chromatogram of FIG. 1 and having a proteolytic activity of the order of 3–5 times that of the protease concentrate, is not contemplated in connection with the practice of this invention. Handling such a powerful protease concentrate would inevitably increase the risk of the occurence of local irritation, particularly of the respiratory tract and other mucous membranes, up to a level which could be unacceptable to enzyme manufacturing plant workers.

Furthermore, the enzymatic instability of such a purified subtilisin component is too high to make such a protease concentrate of any utility as a detergent enzyme. The substantial difference in stability experienced between purified enzyme and commercial protease preparations is apparently due to the presence in the latter of non-enzymatically active culture broth constituents which stabilize the protease. Such stabilizing constituents are at least partly identifiable as smaller peptides and amino acids originating mainly from autodigestion of the protease during its fermentative production. However, additional stabilizing culture broth constituents of an unspecified character may also be present. For the sake of convenience, hereinafter the term "peptide fraction" will be used for these non-proteolytic culture broth constituents. The peptide fraction is eluted together with front peak A when the protease concentrate is fractionated on a CMC ion exchange column as has been described in connection with FIG. 1.

The peptide fraction content is calculated from the formula:

$$\text{percent peptide fraction} = \frac{\text{percent total N} - \text{percent protein N}}{0.14},$$

protein N being the nitrogen content of a trichloroacetic acid precipitate prepared under standardized conditions.

According to a preferred embodiment of the present invention the proteolytic activity of the protease concentrate is in the range of from 2 to 20, preferably from 5 to 15, Anson units (AU) per g, the culture broth derived peptide fraction content therein being in the range of from 2 to 15 percent by weight.

In principle, the objective of providing a process of preparing a protease product essentially free of component C could be achieved by removing only component C from the protease concentrate, e.g. by fractional precipitation and/or selective extraction procedures. However, apart from the fact that no method of this kind has been devised so far, any such method would almost inevitably entail concomitant losses in yield of subtilisin.

In addition, the expenses incurred in carrying out the removal of component C would add substantially to the production costs of the ultimate protease product. The separating approach is unacceptable, as a practical matter.

Likewise, an inevitable rise in production costs to unacceptable levels prohibits any method involving the removal of component C, e.g. by chromatography on a CMC ion exchange column as illustrated in FIG. 1, according to which removal of component C could be effected simply by halting the elution short of the appearance of peak C of the chromatogram.

The above described obstacles to production of a less allergenic protease concentrate have now been overcome in that a process has been devised which essentially eliminates component C at the microbiological level by utilizing a strain of *B. licheniformis* that has been mutated to essentially block the synthesis of component C, whilst retaining fully the ability to synthesize the subtilisin component. Cultures of three such mutant strains of *B. licheniformis* have been deposited with the Northern Regional Research Center, Peoria, Ill., U.S. and have been assigned the following numbers:

NRRL B-11301,
NRRL B-11302, and
NRRL B-11303.

Mutation procedure

Mutation of *B. licheniformis* to block its synthesis of component C whilst retaining its ability to synthesize subtilisin was conducted in the following manner. Logarithmically growing cells on a medium containing Trypticase (2%); yeast extract (0.5%); $FeCl_2$, $6H_2O$ (0.0007%); $MnCl_2, 4H_2O$ (0.0001%); and $MgSO_4, 7H_2O$ (0.0015%) at pH 7.3 and maintained at 30° C. were harvested after 5 hours and suspended in Tris-maleate buffer of pH 5.7.

N-methyl-N'-nitro-N-nitrosoguanidine was added to give a concentration of 100 μg/ml and the suspension was incubated for 30 minutes in a water bath at 30° C. Following this treatment the rate of survival was 0.1%.

The cells were washed several times with the buffer and then spread on agar plates prepared with the above culture medium.

Selection of mutants

After incubation at 37° C. for 2 days excised agar discs, each carrying a mutant colony, were arranged on a glass plate in hexagonal patterns whereafter a 1% agarose gel was poured onto the plate. In a hole, cut out centrally in each hexagon, was placed a sample of component C specific antiserum. The plate was inspected after 1 day's incubation at 30° C. Mutant colonies exhibiting no precipitation lines were selected, purified by subcultivation, and then propagated in shake flasks.

Further characterization of component C Amino acid analysis

The approximate amino acid composition of component C is given below. The determinations are subjected to the usual error of ±10 percent of the values indicated. For comparison, corresponding literature figures of subtilisin itself are indicated in parentheses.

Lys: 10 (9); His: 8 (5); Arg: 11 (4); Asp: 22 (28); Glu: 15 (12); Thr: 33 (19); Ser: 33 (32); Pro: 13 (9); Gly: 37 (35); Ala' 17 (41); Val: 16 (31); Leu (7 (16); Ileu: 15 (10); Phe: 6 (4); Tyr: 21 (13); Cys (½): 2 (0) Met: 3 (5); Trp: not detmd. (1); NH$_3$: 27 (25). Total number of amino acids: 269 (273), excl. Trp.

The amino acid composition of component C is seen to differ significantly from that of subtilisin, the most conspicous difference being the presence of the two cysteine residues (Cys ½) in the former as compared to none in the latter. There are certain indications that the cysteine residues of component C are linked by a disulphide bridge. The presence of an S-S bridge in component C, being a member of the group of Bacillus derived proteases, would be most unusual.

Molecular weight

The amino acid composition figures suggest that the molecular weights of component C and subtilisin are in the same range (the literature figure for the latter being approximately 27.300).

Inhibition studies

Contrary to subtilisin, component C is not inhibited by phosphorylating agents, such as diisopropyl phosphofluoridate (DFP) or phenylmethanesulfonyl fluoride (PMSF). It appears from these observations that component C is not a serine protease.

Furthermore, the fact that component C is not inhibited by chelating agents, such as ethylenediaminetetraacetic acid (EDTA), indicates that it is not a metalloprotease.

Effect of pH on stability

Component C exhibits a lower stability than subtilisin in the pH-range of 9 to 10, the prevailing pH-interval of washing solutions. Apparently this accounts at least partly for the fact that the detergent enzyme properties of component C are appreciably inferior to those of subtilisin.

Allergological studies

Formation of IgE antibodies in rabbits

Solutions (0.5 ml) of each of the test substances subtilisin (15.1 percent protein N) and component C (13.7 percent protein N) together with Alhydrogel (Superfos, Copenhagen, 0.5 ml of 1.3 percent emulsion, calculated as $Al_2O_3$) as adjuvant were injected subcutaneously into rabbits (24 animals in each group). The dosages of the two immunogens under comparison, expressed in µg protein N, were the same. Comparisons were made at 3 dosage levels, corresponding to 0.015, 0.15 and 1.5 µg protein N, respectively.

The animals were bled on the 13th day after the first immunization and then reimmunized the following day. This schedule was repeated each 14th day throughout the entive experimental period of 139 days.

Passive Cutaneous Anaphylaxis (PCA) test

The test was performed according to the procedure described by N. J. Zvaifler et al., Journal of Experimental Medicine vol. 130 (1969) p. 907. Intradermal injections of 0.2 ml of whole serum or serum dilutions were made into the freshly shaven backs of rabbits weighing approx. 2500 g. The tests were performed in triplicate. After a sensitization period of 72 hours the animals were challenged intravenously with antigen+50 mg Ewans Blue (Merck) dissolved in saline (5 ml). The challenge dose corresponded to 750 µg protein N per animal.

The animals were sacrificed after 30–60 minutes with an overdose of Nembutal and the resulting lesions measured and recorded.

At the dosage level of immunogen corresponding to 0.15 µg protein N subcutaneously the positive titers for component C appeared significantly earlier and in a significantly larger proportion of the animals than did those for subtilisin.

At the same dosage level the sum of titer levels induced by component C over 10 bleedings was significantly higher than that of subtilisin ($P<0.02$). Likewise,, component C reached significantly higher maximum titers ($P<0.02$).

Modified Anson-hemoglobin method for the determination of proteolytic activity In the Anson-hemoglobin method for the determination of proteolytic activity, denatured hemoglobin is digested under standard conditions. The undigested hemoglobin is precipitated with trichloroacetic acid (TCA) and the amount of TCA soluble product is determined with Folin-Ciocalteu phenol reagent.

One Anson unit (AU) is the amount of enzyme which under standard reaction conditions digests hemoglobin at such an initial rate that there is liberated per minute an amount of TCA soluble product which gives the same colour with phenol reagent as one milliequivalent of tyrosine.

The standard reaction conditions are the following: Temperature 25° C.; reaction time 10 min.; pH 7.5.

For further reference, vide: M. L. Anson, Journal of General Physiology vol. 22 (1939), pp. 79–89; O. Folin and V. Ciocalteu, The Journal of Biological Chemistry vol. 73, (1927), pp. 627–636.

The invention will now be described in further detail with rereference to the following examples:

EXAMPLE 1 .

Each of the B. licheniformis strains NRRL B-11301, B-11302 and B-11303 were cultivated under the following conditions:

Baffled Erlenmeyer flasks (500 ml) were prepared with substrate (100 ml) in each. The following substrate compositions were used

|  | Substrate 1 percent (w/v) | Substrate 2 percent (w/v) | Substrate 3 percent (w/v) |
| --- | --- | --- | --- |
| Potato starch | 10 | 12.5 | 10 |
| Soy bean meal | 5 | 7.5 | 2 |
| $Na_2HPO_4 . 12H_2O$ | 1 | 0.5 | 1 |
| Pluronic L-61 | 0.01 | 0.01 | 0.01 |
| Tween 80 |  | 1 |  |
| Barley starch |  |  | 5 |
| Sodium caseinate |  |  | 1 |
| BAN 120 L | 0.01 | 0.01 | 0.01 |

Pluronic L-61 is a non-ionic surfactant distributed by Wyandotte Corporation, Michigan, U.S.A.

Tween 80 is polyoxyethylene sorbitan monooleate distributed by Atlas Chemical Industries, Delaware, U.S.A.

BAN 120 L is a commercial alpha-amylase product, obtained by fermentation of B. subtilis, and supplied by Novo Industri A/S, Denmark.

The media were heated from 50° to 90° C. in the course of 50 min., then heated to 121° C. for an additional 80 min., followed by cooling.

The flasks were inoculated with the B. licheniformis strain and then shaken on a rotary shaking table at 240 r.p.m. for five days at 30° C. The protease activity was then determined by the Anson method. The following results were obtained (AU/kg):

| Strain | Substrate 1 | Substrate 2 | Substrate 3 |
|---|---|---|---|
| NRRL B-11301 | 160 | 219 | 153 |
| NRRL B-11302 | 158 | 200 | 155 |
| NRRL B-11303 | 161 | 192 | 150 |

Samples of the culture broths obtained as described above using substrate 2 were centrifuged at 15,000 g for 30 min. The supernatant was separated and 50 ml aliquots were warmed to 37° C. Anhydrous $Na_2SO_4$ (15 g) was added to each portion and the mixture was stirred for 30 min. The precipitate was then filtered off and dried under vacuum.

The resulting protease concentrates had the following characteristics:

| Strain | Proteolytic activity AU/g | Protein content percent | Peptide fraction percent |
|---|---|---|---|
| B-11301 | 11 | 34 | 8 |
| B-11302 | 10 | 35 | 10 |
| B-11303 | 10 | 31 | 8 |

A sample (5 g) of the product obtained from *B. licheniformis* NRRL B-11301 was chromatographed on a column (25×23.5 cm) of CMC (130 g) under conditions analogous to those described previously. The chromatogram was obtained by monitoring $OD_{280}$ of fractions (20 ml) collected at a flow rate of 45 ml/h.

Figure 3:
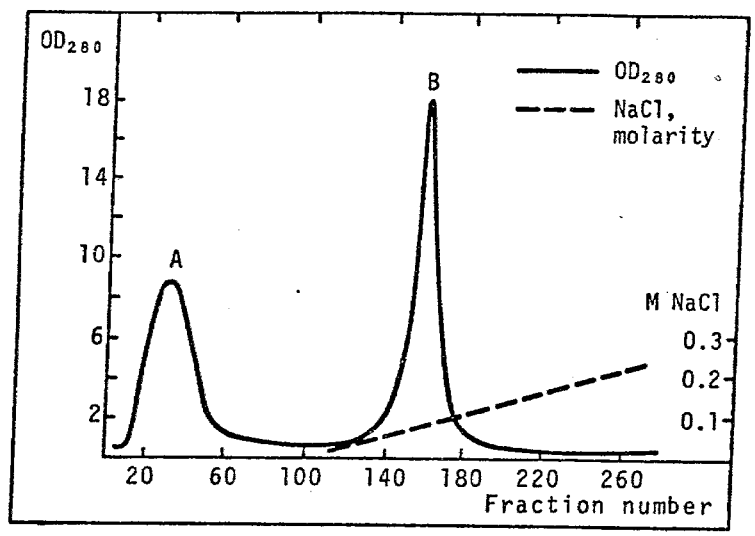
Figure 4:
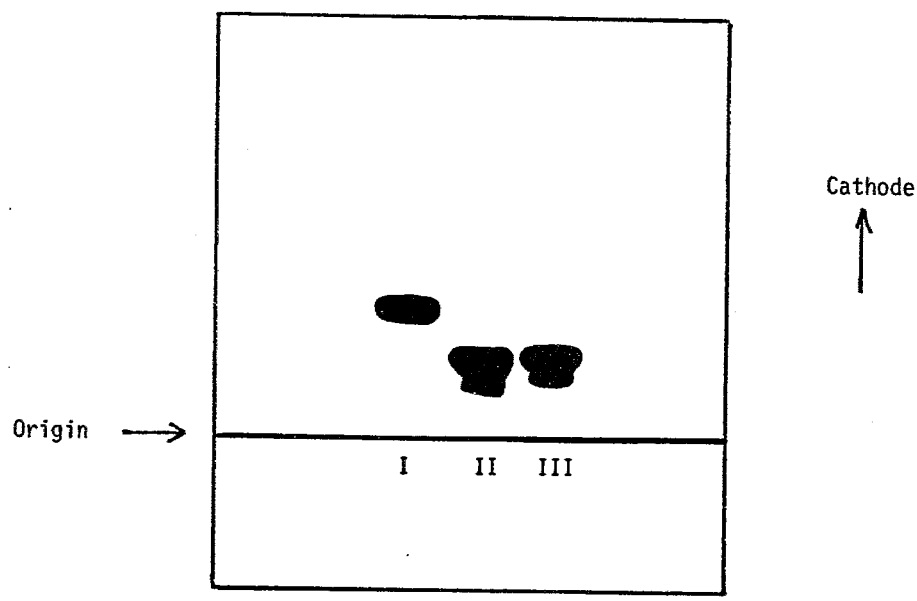

In addition, a solution (3% w/w) of the same concentrate was subjected to agarose gel electrophoresis according to the method described previously. Solutions (1% w/v) of subtilisin and component C were applied as references. The chromatogram and electropherograms, shown in FIGS. 3 and 4, respectively of the accompanying drawings, demonstrate that the only protease detectable in the protease concentrate (FIG. 4, position III) is subtilisin (position II), while component C (Position I) is absent.

EXAMPLE 2

*B. licheniformis* strain NRRL B-11301 was grown on nutrient agar for 1-2 days at 37° C. in a Fernbach flask. The culture was then propagated in a stainless steel fermentation tank, containing the fermentation substrate described below. After 24 h at 34° C. with aeration and stirring a dense culture was obtained. This culture was then used to seed the enzyme production tank. The seed culture (35 l) was transferred to a stainless steel fermentation tank containing the fermentation substrate described below. Fermentation conditions for both the seed tank and the main tank were as follows:

| | |
|---|---|
| Total tank volume: | 550 l |
| Substrate volume: | 350 l |
| Rate of aeration: | 300 l/min. |
| Stirring: | 400 rpm with a six-bladed turbine stirrer, 28 cm diameter |
| Temperature: | 34° C. |
| Substrate composition: | |
| Potato starch | 100 g/l |
| Soy bean meal | 50 g/l |
| $Na_2HPO_4 \cdot 12H_2O$ | 10 g/l |
| BAN 120 L | 0.1 ml/l |
| Pluronic L-61 | 1 g/l |

Substrate preparation

The substrate was heated from 50° to 95° C. in the course of 50 min., and then sterilized at 121° C. for 60 min.

After a fermentation time of 50 h, the protease activity was 160 AU/kg, as determined by the modified Anson method. The fermentation broth was then cooled to about 5° C.

a.

A sample of the culture broth from the fermentation described above was centrifuged at 15.000 g for 30 min. The supernatant was separated and then warmed to 37° C. Anhydrous $Na_2SO_4$ (320 g/l) was added and the mixture was then stirred for 30 min., still maintained at 37° C. The precipitate was then filtered off and dried under vacuum.

The resulting protease concentrate had the following characteristics:

| | |
|---|---|
| Proteolytic activity | 8 AU/g |
| Protein content | 20 percent |
| Peptide fraction | 4 percent |

Chromatography on CMC and agarose gel electrophoresis, conducted in the same manner as described in Example 1, demonstrated that the protease product was free of component C, the only detectable protease being subtilisin.

b.

A second aliquote of the above culture broth was centrifuged at 15.000 g for 30 minutes. The supernatant was then separated off. Acetone (3 volumes) was added slowly and with vigorous stirring to the supernatant. The resulting precipitate was then filtered off and dried under vacuum.

The resulting protease concentrate had the following characteristics:

| | |
|---|---|
| Proteolytic activity | 6 AU/g |
| Protein content | 15 percent |
| Peptide fraction | 3 percent |

Chromatography on CMC and agarose gel electrophoresis, conducted in the same way as described in Example 1, demonstrated that the protease product was free of component C, the only detectable protease being subtilisin.

EXAMPLE 3

A commercial, particulate protease product was prepared in the following manner:

A pre-mix consisting of enzyme concentrate (8 AU/g, 25% by weight) prepared as described in Example 2a, polyvinylpyrrolidone (2%), polyethylene glycol 6000 (6%) and sodium chloride (67%) was moistened with water (8%), extruded through a screen with 0.9 mm holes and then spheroidized as described in British Pat. No. 1,362,365. The particulate product was dried on a fluidized bed to a moisture content of about 0.5% following by coating with polyethylene glycol (4% by weight) and finally powdered with a mixture (11%) of titanium dioxide and magnesium silicate. The final enzyme preparation had an activity of 1.7 AU/g.

EXAMPLE 4

A granular protease product was prepared substantially as described in U.S. Pat. No. 4,106,991.

Finely ground protease concentrate (9 AU/g, 25% by weight) prepared according to Example 2a, titanium dioxide (2%), cellulose powder (10%) CEPO S20 (The Swedish Cellulose Powder and Wood Flour Mills, Ltd.), and finely ground sodium chloride (62%) were mixed in a Lödige mixer as described in Example 1 of the above U.S. patent.

The dry mixture was sprayed with a 4.5% aqueous solution of polyvinylpyrrolidone K 30 (1% by weight of the total mixture) functioning as a binder. Granulation of the product was performed in the Lödige mixer followed by drying of the granular product to a moisture content below 3%. Finally, the granules were sieved and then coated with polyethylene glycol and powdered according to the procedure described in Example 3. The protease preparation so obtained had an activity of 2 AU/g.

EXAMPLE 5

The particulate protease products prepared according to Example 3 and 4 were used for the preparation of washing powder compositions of the following formulations:

| a. Constituent | Amount (percent by weight) |
| --- | --- |
| NANSA S 4c S | 10 |
| Berol WASC | 4 |
| Soap | 3 |
| Sodium tripolyphosphate | 30 |
| Sodium perborate | 25 |
| Sodium silicate | 6 |
| Sodium CMC | 1 |
| Optical brighteners, perfumes | 0.5 |
| pH adjusting agents | as needed |
| Protease product (1.5–2.0 AU/g) | 0.8 |
| Sodium sulphate, balance to | 100 |

| b. Constituent | Amount (percent by weight) |
| --- | --- |
| NANSA S 40 S | 10 |
| Berol WASC | 4 |
| Soap | 3 |
| Sodium tripolyphosphate | 15 |
| SASIL | 15 |
| Sodium perborate | 25 |
| Sodium silicate | 6 |
| Sodium CMC | 1 |
| Optical brighteners, perfumes | 0.5 |
| pH adjusting agents | as needed |
| Protease product (1.5–2.0 AU/g) | 0.8 |
| Sodium sulphate, balance to | 100 |

NANSA S 40 S is a sodium alkyl benzene sulphonate, based on "soft" fully biodegradable alkylate, in powder form (Marchon Ltd).

Berol WASC is a non-ionic alkyl phenyl polyglycol ether (Berol A/B).

SASIL is a sodium aluminum silicate zeolite of type A with the formula $Na_{12}(AlO_2)_{12}(SiO_2)_{12}\cdot 27H_2O$ (Degussa).

What is claimed is:

1. A protease preparation having therein a *B. licheniformis* derived protease concentrate, wherein said protease concentrate:
    is stabilized by the presence therein of at least 0.5 percent by weight thereof of non-proteolytic peptides from the culture broth wherein the protease was generated;
    is essentially free of non-serine protease; and,
    exhibits substantially attenuated allergenic properties as compared to a non-serine protease containing *B. licheniformis* protease concentrate.

2. The protease preparation of claim 1, in which at least 99 percent of the proteolytic activity of the protease concentrate incorporated therein is derived from the subtilisin isoenzyme system.

3. The protease preparation of claim 1, in which the protease concentrate contains therein 2–15 percent by weight of nonproteolytic culture broth derived peptides.

4. The protease preparation of claim 1, in which the proteolytic activity of the protease concentrate is in the range of from 2 to 20 Anson units per g.

5. A process for preparing a protease concentrate suitable for incorporation into the protease preparations adapted for admixture into washing compositions, said protease concentrate being essentially free of non-serine protease and exhibiting substantially attenuated allergenic properties as compared with a non-serine protease containing protease concentrate, characterized in that a strain of *B. licheniformis*, mutated to essentially block its capability for synthesizing other proteases than subtilisin, is cultivated in a nutrient medium containing assimilable sources of carbon, nitrogen and phosphorus, followed by recovery of the protease concentrate comprising subtilisin and culture broth derived peptides.

6. The process of claim 5, in which the mutated *B. licheniformis* strain is selected from strains having been assigned deposit numbers NRRL B-11301, B-11302, and B-11303.

* * * * *